(12) United States Patent
Meisenberg et al.

(10) Patent No.: US 10,008,064 B2
(45) Date of Patent: Jun. 26, 2018

(54) MEASURING DEVICE FOR MEASURING MAGNETIC PROPERTIES OF THE SURROUNDINGS OF THE MEASURING DEVICE

(71) Applicant: MEAS Deutschland GmbH, Dortmund (DE)

(72) Inventors: Armin Meisenberg, Dortmund (DE); Axel Bartos, Waltrop (DE); Reinhold Pieper, Lüdinghausen (DE)

(73) Assignee: TE Connectivity Sensors Germany GmbH, Dortmund (DE)

( * ) Notice: Subject to any disclaimer, the term of this patent is extended or adjusted under 35 U.S.C. 154(b) by 59 days.

(21) Appl. No.: 14/759,127

(22) PCT Filed: Dec. 30, 2013

(86) PCT No.: PCT/EP2013/003923
§ 371 (c)(1),
(2) Date: Jul. 2, 2015

(87) PCT Pub. No.: WO2014/106534
PCT Pub. Date: Jul. 10, 2014

(65) Prior Publication Data
US 2015/0348349 A1    Dec. 3, 2015

(30) Foreign Application Priority Data
Jan. 2, 2013 (DE) .......... 10 2013 000 016

(51) Int. Cl.
*G01R 33/02* (2006.01)
*G07D 7/04* (2016.01)
(Continued)

(52) U.S. Cl.
CPC .............. *G07D 7/04* (2013.01); *G01R 15/20* (2013.01); *G01R 33/0206* (2013.01);
(Continued)

(58) Field of Classification Search
CPC .. B64G 1/366; G01R 33/0206; G01R 33/028; G01R 33/038; G01R 33/1215;
(Continued)

(56) References Cited

U.S. PATENT DOCUMENTS 7,548,060 B2   6/2009   Herrmann et al.
8,910,869 B2   12/2014  Schutzmann et al.
(Continued)

FOREIGN PATENT DOCUMENTS

DE        2834287 A1    2/1980
DE    102004011809 A1    9/2005
(Continued)

OTHER PUBLICATIONS

International Search Report from international Application No. PCT/EP2013/003923 dated Apr. 17, 2014.
(Continued)

*Primary Examiner* — Huy Q Phan
*Assistant Examiner* — Raul Rios Russo
(74) *Attorney, Agent, or Firm* — Howard IP Law Group, PC

(57) ABSTRACT

A measuring device for measuring magnetic properties in a vicinity of the measuring device, in connection with a sensor line having sensor elements, includes a magnetization device for generating a magnetic field substantially homogeneous in a region of the sensor line, the field direction of the magnetic field, in the region of the sensor line, being at an angle of greater than 0° and less than 90° to the direction of the sensor line.

19 Claims, 8 Drawing Sheets

(51) Int. Cl.
*G01R 33/06* (2006.01)
*G01R 33/038* (2006.01)
*G01R 33/38* (2006.01)
*G01R 33/028* (2006.01)
*G01R 15/20* (2006.01)
*G01N 27/90* (2006.01)

(52) U.S. Cl.
CPC ....... *G01R 33/028* (2013.01); *G01R 33/0283* (2013.01); *G01R 33/038* (2013.01); *G01R 33/06* (2013.01); *G01R 33/38* (2013.01); *G01N 27/90* (2013.01)

(58) Field of Classification Search
CPC .... G01R 15/20; G01R 33/0283; G01R 33/38; G01N 27/90; G11C 19/085
USPC ................. 324/51, 55, 200, 227, 228, 244
See application file for complete search history.

(56) References Cited

U.S. PATENT DOCUMENTS

| | | |
|---|---|---|
| 9,482,725 B2 | 11/2016 | Bartos et al. |
| 2007/0222441 A1* | 9/2007 | Satoh ................ G01R 33/0206 324/253 |
| 2011/0043193 A1* | 2/2011 | Aebi ....................... G01D 5/145 324/207.2 |
| 2011/0148408 A1* | 6/2011 | Meisenberg ........... G01R 33/09 324/252 |
| 2011/0309829 A1* | 12/2011 | Loreit ..................... G01D 1/00 324/252 |
| 2013/0099777 A1* | 4/2013 | Heberle .................. G01B 7/14 324/207.2 |
| 2013/0106410 A1* | 5/2013 | Liu .................... G01R 33/0029 324/246 |
| 2013/0200887 A1* | 8/2013 | Bartos ...................... G01B 7/14 324/207.24 |
| 2013/0328556 A1* | 12/2013 | Granig ................ G01R 33/093 324/252 |
| 2014/0312894 A1* | 10/2014 | Bartos ................. G01R 33/091 324/252 |

FOREIGN PATENT DOCUMENTS

| | | |
|---|---|---|
| DE | 102004063539 A1 | 9/2005 |
| DE | 102011106263 A1 | 12/2011 |
| DE | 102010035469 A1 | 3/2012 |
| DE | 102011110138 A1 | 2/2013 |
| RU | 2458404 C2 | 8/2012 |
| WO | 98/38792 A1 | 9/1998 |
| WO | 2009027771 A1 | 3/2009 |

OTHER PUBLICATIONS

German Office Action from German Application No. DE2013000016.5 dated Sep. 10, 2013.

* cited by examiner 3a  3b                 2    1
4

Line direction Z

MEASURING DEVICE FOR MEASURING MAGNETIC PROPERTIES OF THE SURROUNDINGS OF THE MEASURING DEVICE

CROSS REFERENCE TO RELATED APPLICATION

The present patent application is the national stage application under 35 U.S.C. § 371 of International Application No. PCT/EP2013/003923 filed Dec. 30, 2013, and claims priority under 35 U.S.C. § 119 to German patent application 10 2013 000016.5 filed Jan. 2, 2013, the entire disclosures of which are incorporated herein by reference in their entireties.

BACKGROUND

The invention relates to a measuring device for measuring magnetic properties of the surroundings of the measuring device with a sensor line with at least two sensor elements extending in a line direction. The invention also relates to a use of such a measuring device.

A possible area of application of the invention is the examination of notes or paper sheets, in particular banknotes, cheques and other paper sheets for the presence of magnetic features, in particular to establish whether the notes or paper sheets have particular, previously fixed magnetic features. Security documents can comprise soft-magnetic security features and/or hard-magnetic security features. Hard-magnetic security features can be produced from materials with high remanence and high coercive field strength. Soft-magnetic security features can be produced from materials with high remanence, but low coercive field strength. Permanent magnets are produced in particular from hard-magnetic materials. Soft-magnetic materials are ferromagnetic materials, which can easily be magnetised in a magnetic field. The associated magnetic polarisation (magnetisation) can be generated for example by a current in a current-carrying coil or by the presence of a permanent magnet. A polarisation thus generated leads in a soft-magnetic material to a magnetic flux density which is many times higher than the externally acting magnetic field generates in the air. Soft-magnetic materials usually have a coercive field strength of less than 1000 A/m. Soft-magnetic materials can however certainly possess saturation magnetisation values comparable with hard-magnetic materials, so that they cannot be distinguished in the saturated state from hard-magnetic materials.

To verify soft-magnetic security features in a security document, therefore, an external magnetic field must be present which saturates the soft-magnetic materials as far as possible. Large magnets are incorporated in measuring devices known from practice, which large magnets generate a sufficiently strong field for the magnetisation of the soft- and hard-magnetic security features, but which also make the structure of such measuring devices complicated. It is known from DE 696 08 137 T2 to provide a reading head, which comprises magnetisation means and at least one magnetoresistive element, wherein the magnetoresistive element has a variable resistance, which is dependent on the magnetic flux applied to it. The reading head described there is used in such a way that each security document is to be identified during the relative movement of the security document with respect to the reading head is first passed in front of the magnetisation means and then in front of said magnetoresistive element, wherein the magnetisation means can be designed in such a way that a constant magnetic flux is present at the sensor element.

A magnetic field emerges from hard-magnetic security features by itself alone and without the presence of an external magnetic field, if the hard-magnetic materials have previously been completely and unequivocally magnetised. This magnetic field continues to be present even over a fairly long time. In the course of time, however, statistical processes have an effect such that the hard-magnetic materials can become demagnetised. For example, banknotes often experience knocks or get creased when they are handled. This can lead to a demagnetisation of the hard-magnetic materials. For the measurement of hard-magnetic security features, it is therefore expedient to imprint a new (unequivocal and durable) magnetisation on the hard-magnetic security feature by means of a premagnetisation magnet. This newly imprinted magnetisation is then able to maintain the hard-magnetic security feature over a longer period, at least over the period of the measurement.

DISCUSSION OF THE RELATED ART

A particular security feature on banknotes is the ferromagnetic security thread (see DE 16 96 245 A1). In practice, ferromagnetic materials are for example used to form the security thread, but they can however have both a low coercive field strength and a high coercive field strength. In a particularly preferred embodiment, therefore, measuring devices for examining such banknotes are designed to identify both security threads made of material with low coercive field strength as well as security threads made of material with high coercive field strength.

In this area of application, it is known from EP 0 977 015 A2 to provide a measuring device for measuring magnetic properties of the surroundings of the measuring device with a sensor line with two sensor elements extending in a line direction. The sensor line can measure the magnetic properties of its surroundings. The measuring device described there comprises a premagnetisation magnet, which generates in the sensor elements a magnetic field which is essentially homogeneous and the field direction whereof in the region of the sensor line points in the line direction. Furthermore, a premagnetisation magnet is provided with the measuring device provided there. This premagnetisation magnet enhances the hard-magnetic security features of a document to be examined in a way such that it strengthens the field emerging from the hard-magnetic security features. The premagnetisation magnet is arranged spaced apart from the sensor line and should be shielded with respect to the sensor line, so that the magnetic field generated by the premagnetisation magnet does not act on the sensor elements of the sensor line. Furthermore, EP 0 977 015 A2 teaches, for the magnetoresistive elements to be used to form the sensor elements, the use of ones such as those which have a V-shaped characteristic of their impedance variation in relation to variations of an external field pointing in the line direction.

A measuring device for measuring magnetic properties of the surroundings of the measuring device with a sensor line with at least two sensor elements extending in a line direction is known from EP 1 701 176 A1, wherein the sensor line can measure the magnetic properties of its surroundings. In the design known from EP 1 701 176 A1, two magnetoresistive sections are provided on a magnetoresistive element. The individual magnetoresistive elements are arranged in a row and form the sensor line. Each magnetoresistive element comprises a support field magnet. According to the embodiment shown in FIGS. 9a and 9b of EP 1 701 176 A1, an essentially homogeneous magnetic field is generated by the support field magnets, the field direction whereof in the region of the sensor line is orientated at an angle of 90° with respect to the line direction. According to the examples of embodiment represented in FIGS. 3a, 3b, FIGS. 4a, 4b, FIGS. 5a, 5b and according to the example of embodiment represented in FIG. 6, the support field magnets generate an inhomogeneous field in the region of the sensor line.

It is also known from WO 2010/006801 A1 to constitute a measuring device for measuring magnetic properties of the surroundings of the measuring device with a sensor line with at least two sensor elements extending in a line direction, wherein the sensor line can measure the magnetic properties of its surroundings. In the figures of WO 2010/006801 A1, a support field device is shown, which comprises individual magnets and which generates an inhomogeneous field in the region of the sensor line. WO 2010/006801 A1 teaches adjusting the course of the field strength in the line direction in a particular way with regard to the sensor elements.

A measuring device for measuring magnetic properties of the surroundings of the measuring device with a sensor line with at least two sensor elements extending in a line direction is known from DE 10 2011 110 138. The magnetic properties of the surroundings of the sensor line can be measured with the sensor line. The measuring device described there comprises a support field device, which generates a magnetic support field in the region over which the sensor line extends. Furthermore, the previously known measuring device comprises a premagnetisation device, which comprises a premagnetisation magnet or a plurality of premagnetisation magnets, wherein at least one premagnetisation magnet is arranged spaced apart from the sensor line in a direction perpendicular to the line direction and extends in a direction parallel to the line direction. The previously known measuring device proposes a particular coordination of the premagnetisation device with the support field device, so that a special overlapping magnetic field arises from the overlap of the magnetic field generated by the premagnetisation device and the support field, the strength of the field component whereof pointing in the line direction is greater at at least one site on the sensor line than the strength of the field component pointing perpendicular to the line direction and not in the direction of the height of the sensor element.

Premagnetisation devices and support field devices are described in the measuring devices known from WO 2010/006801 A1, DE 10 2011 110 138 A1 and EP 0 977 015 A2. In the design known from EP 0 977 015 A2, the premagnetisation device is constituted separate from the support field device, wherein the support field device is constituted by a single magnet with a north pole and a south pole. In the measuring device known from WO 2010/006801 A1, the support field device comprises a line of magnets arranged beside one another in the line direction of the sensor elements. The magnetisation of the magnets of this line can be alternating or can be constituted in an alternative embodiment such that the magnetisation of the individual magnets of the support field device has the same direction.

In the measuring device known from DE 10 2011 110 138 A1, a premagnetisation device constituted separate from the support field device is provided. The support field device can comprise one or more components, for example permanent magnets, and can be constituted for example by a single magnet with a locally varying magnetisation distribution.

The measuring devices known from the prior art are either complex in their structure on account of the large number of individual components to be used, in particular when a plurality of permanent magnets is to be used, or they have a relatively large space requirement. Applications are known in which a measuring device is to be used to measure magnetic properties of the surroundings of the measuring device, said measuring device being intended to measure reliably the magnetic properties of the surroundings of the measuring device, but being intended to be constituted compact and/or simple. The problem underlying the invention, therefore, is to propose precisely one such measuring device.

SUMMARY

The invention proceeds from the basic idea of generating a magnetic field with a magnetisation device, said magnetic field being essentially homogeneous in the region of the sensor line and its field direction in the region of the sensor line pointing at an angle of greater than 0° and less than 90° with respect to the line direction.

This offers the advantage that the invention can be implemented for example with a single magnet, which acts both as a premagnetisation magnet and also as a support field magnet. The field component orientated perpendicular to the line direction is able to assume the premagnetisation, i.e. the saturation of the soft-magnetic structures, from the field direction of the magnetic field of the magnetisation device which runs obliquely with respect to the line direction. The field component of the magnetic field generated by the magnetisation device pointing in the line direction can assume the functions of a support field magnet. Due to the fact that the invention makes it possible to implement the functions of the premagnetisation magnet and the functions of the support field magnet by means of one magnet, the embodiment according to the invention can be implemented in a compact form and with few components, in particular with few magnets.

The invention proceeds from the basic idea of generating an essentially homogeneous field in the region of the sensor line. The region of the sensor line is understood to mean, in particular, the spatial region which just still encloses the sensor elements of the sensor line.

The measuring device according to the invention is suitable for measuring magnetic properties of the surroundings of the measuring device. Magnetic properties of the surroundings of the measuring device are understood in particular to mean the magnetic field strength of a magnetic field in the surroundings of the measuring device, the field direction of a magnetic field in the surroundings of the measuring device or for example the change in the field strength or field direction of a magnetic field in the surroundings of the measuring device. For example, a magnetic property of the surroundings is understood to mean the change in the field strength or the field direction of the magnetic field surrounding the measuring device, when this field changes due to the overlapping of a field which is generated by a magnetic pattern of a banknote. In a preferred embodiment, the sensor line is constituted such that it detects only spatial and/or temporal changes in the magnetic properties of the surroundings of the measuring device.

In a preferred embodiment, the sensor element or an interconnection of sensor elements is constituted such that it can measure magnetic properties of the surroundings of the measuring device, which by definition also includes the change in a field strength, only in one direction of an orthogonal coordinate system, said direction being referred to as the measurement direction, or in an alternative embodiment can measure the aforementioned only in two directions of an orthogonal coordinate system which lie in a plane referred to as the sensor measurement plane.

In a preferred embodiment, the measuring device according to the invention is constituted for measuring magnetic structures of a note or a paper sheet, in particular a banknote or cheque, and comprises suitable means for moving the note or paper sheet past the sensor line in a measurement plane at least in a region close to the sensor line. The direction in which the note or the paper sheet is moved is referred to as the reading direction. The sensor element is particularly preferably constituted such that the measuring direction corresponds to the reading direction, i.e. the sensor element can only measure magnetic properties of its surroundings in the reading direction. If the sensor element, or an interconnection of sensor elements, is constituted such that it can read magnetic properties of the surroundings of the measuring device only in two directions of an orthogonal coordinate system which lie in a plane referred to as the sensor measurement plane, the measurement plane in which the note or the paper sheet is moved past the sensor line is arranged particularly preferably parallel to the sensor measurement plane.

A sensor line is provided with at least two magnetoresistive sensor elements extending in a line direction in the measuring device according to the invention. The sensor element can be constituted for measuring the magnetic properties in its surroundings in particular in such a way that it exhibits the "anisotropic" magnetoresistive effect (AMR effect) or the "giant" magnetoresistive effect (GMR effect). The sensor element can however also exhibit other effects, such as for example the giant magnetoimpedance effect (GMI), the tunnel magnetoresistance effect (TMR) or the Hall effect.

A sensor element particularly preferably comprises four or more individual bridge resistors connected together to form a Wheatstone bridge or two or more individual bridge resistors connected together to form a half Wheatstone bridge. A sensor element can however also be constituted by a single resistor, wherein in such an embodiment a plurality of sensor elements (individual resistors) are preferably connected together to form a Wheatstone bridge or a half Wheatstone bridge.

In a preferred embodiment, the sensor element, or a plurality of sensor elements connected together, can be used to constitute a sensor according to the gradient principle. In a gradient sensor, two spaced-apart sensor elements are interconnected in such a way that a local field difference between the two sensor elements generates a measurement signal, whereas a field acting equally on both sensor elements does not cause any signal change. In an alternative embodiment, the sensor element is constituted or sensor elements connected together are constituted such that they constitute a homogeneous field sensor. In a homogeneous field sensor, the sensor elements are interconnected in such a way that the generated signal is proportional, to a first approximation, to the mean value of the field strength acting on the individual sensors, whereas local field differences between the individual sensor elements do not generate any sensor signals. Since a homogeneous field sensor can, compared to the gradient sensor, have much smaller dimensions in the direction of movement and the dimensions of the sensitive area determine the resolution capacity, a higher detail resolution in the direction of movement can usually be achieved with a homogeneous field sensor.

The sensor element has a width and a length and a height, wherein the height is preferably smaller than the width and the height is preferably smaller than the length and the line direction preferably points in the direction of the width or in the direction of the length of the sensor element.

The sensor line comprises at least two sensor elements, which are arranged in the line direction one behind the other. The length of the sensor line and therefore the number of magnetoresistive sensor elements used depends on the measurement to be carried out. For the measurement of Euro banknotes, a sensor line can for example comprise more than 10, particularly preferably more than 20, for example more than 31 and preferably 90 sensor elements, especially when the device is used to measure Euro banknotes which are moved with their short side in a measurement direction relative to the measuring device. In a preferred embodiment, however, only 10 or less than 10, particularly preferably 9 sensor elements are provided in the direction of the sensor line. This enables a short measuring device to be constructed in the line direction. Areas of application are known in which it is to be verified whether a measurement object moved past the measuring device has previously determined magnetic properties at a specific site. In these areas of the application, it is possible to move the measurement object past the measuring device in such a way that the partial segment of the measurement object giving rise the magnetic properties to be ascertained can be moved past the measuring device inside a clearly defined region. This allows the measuring device to be constituted narrow. For example, the extension in the line direction can correspond to the tolerance range within which the partial segment of the measurement object giving rise to the properties to be verified is definitively passed. If the measuring device does not detect any change in the magnetic properties of its surroundings that corresponds to such a partial segment being passed by, then it is established that the measurement object to be examined does not possess the magnetic properties to be verified. A measuring device which can be produced in a compact form and in a straightforward manner and which is therefore usually cost-effective is particularly well suited for such applications.

To form the sensor line, the sensor elements—insofar as present—are arranged in a line. The sensor elements particularly preferably lie on a line. It is however also conceivable for the sensor elements of a single line to be arranged differently in relation to an axis pointing in the line direction, so that the longitudinal central axes of the individual sensors no longer all lie on a line. Particularly preferably, however, sensor elements arranged in this way are arranged such that they partially overlap as viewed in the direction of the line direction.

In a preferred embodiment, a plurality of sensor elements is combined to form a subassembly, for example arranged on a common support structure, typically a chip. Such a subassembly, if it is mounted directly on a printed-circuit board, or alternatively a solderable electronic housing with an incorporated chip, is referred to in the following as a sensor. In an embodiment, the sensor is arranged directly on the magnet. A sensor can for example be constituted by the fact that a chip comprises a plurality of sensor elements. A sensor can for example comprise two, three, four or more sensor elements. It is however also possible for a sensor to be constituted by a single sensor element.

The basic idea of the invention is based on generating a magnetic field with the magnetisation device, which field is essentially homogeneous in the region of the sensor line and the field direction whereof in the region of the sensor line lies at an angle greater than 0° and less than 90° with respect to the line direction. The magnetic field generated by the magnetisation device is the magnetic field which acts on the sensor line when, with the exception of the natural magnetic fields always acting, no further magnetic field acts on the sensor line, i.e. the sensor line is not yet located at its measurement site. A further magnetic field can overlap this magnetic field generated by the magnetisation device at the measurement site, for example when a security document to be verified is passed by the sensor line. This overlapping of the two fields is for example the change in the field strength or field direction defined above as a magnetic property of the surroundings.

In a preferred embodiment, the field direction of the magnetic field generated by the magnetisation device is orientated more perpendicular than parallel with respect to the field direction, i.e. it forms an angle greater than 45° with respect to the line direction. In the majority of applications, the field component required to support the sensor elements, i.e. the field component of the magnetic field pointing in the line direction, is smaller than the field strength required for the premagnetisation and in particular for the saturation of soft-magnetic structures, i.e. the field strength of the field component of the magnetic field of the magnetisation device pointing perpendicular to the line direction. In a preferred embodiment, therefore, the angle between the field direction of the magnetic field of the magnetisation device in the region of the sensor line is greater than 45° with respect to the line direction. A field angle in the range between 65° and 85° is particularly preferable. Since, when use is made of AMR sensors, the support field strength in the line direction acts in a sensitivity-determining manner, a very great dependence of the sensor sensitivity on residual, design-related and production-related field angle variations can exist in the case of excessively steep angles, whilst the sensor sensitivity is excessively low in the case of flat angles.

The magnetic field generated by the magnetisation device can be used to saturate soft-magnetic structures and thus to bring them into a state such that their presence on the measurement object to be examined can be detected by the sensor line. The magnetic field of the magnetisation device can however also be used to saturate hard-magnetic structures in a defined manner, in order to generate a sensor signal independent of earlier magnetisations.

In a preferred embodiment, the sensor line has a length, a width and a height, wherein the height is less than the width and a height is less than the length, and wherein the magnetic field generated by the magnetisation device in the region of the sensor line has essentially only one field component in the direction of the length of the sensor line and one field component in the direction of the height of the sensor line, but in the region of the sensor line essentially no field component in the direction of the width of the sensor line. In this preferred embodiment, sensor elements or interconnections of sensor elements are in particular used that are based on a magnetoresistive effect and are constituted such that they detect the magnetic field component in only one measurement direction, preferably the direction pointing perpendicular to the line direction and not in the direction of the height. For example, use can be made of magnetoresistive sensors which are produced in planar thin-layer technology and which are virtually insensitive to the field component perpendicular to the chip plane. If the magnetic field of the magnetisation device is adjusted such that it has essentially no field component in the direction of the width of the sensor line, use can be made of sensors which are sensitive only in this measurement direction (in the direction of the width of the sensor line), without their being disturbed by the magnetic field of the magnetisation device.

In a preferred embodiment, the sensor elements constituting the sensor line are arranged and constituted in such a way that they can measure the magnetic properties of the surroundings essentially only in the line direction. In an alternative embodiment, the sensor elements constituting the sensor line are arranged and constituted in such a way that they can measure the magnetic properties of the surroundings essentially only in a direction which is not the line direction and not the direction of the height of the sensor line. Once again in an alternative embodiment, the sensor elements constituting the sensor line are arranged and constituted in such a way that they can measure the magnetic properties of their surroundings essentially only in a plane referred to as the sensor plane and spanned by two perpendicular measurement directions of an orthogonal coordinate system, wherein the line direction is one of these measurement directions and the direction of the width of the sensor line is the second of these measurement directions.

In a preferred embodiment, the magnetisation device comprises a first magnet, which is arranged in the line direction in the region of the one end of the sensor line, and a second magnet which is arranged in the line direction in the region of the opposite end of the sensor line. In this embodiment, the lines connecting the north pole to the south pole are orientated at an angle greater than 0° and less than 90° with respect to the line direction both in the case of the first magnet and in that of the second magnet. To improve the field homogeneity perpendicular to the line length direction, it may be expedient for each of the two previously described magnets to be split up for its part into two magnets spaced apart.

In an alternative embodiment, the magnetisation device comprises a single magnet. In a particularly preferred embodiment, the magnet extends at least over the entire length of the sensor line in the line direction. The magnet is preferably arranged such that the line connecting its north pole to its south pole runs at an angle greater than 0° and less than 90° with respect to the line direction. The line connecting the north pole and south pole does not necessarily have to be arranged at the same angle relative to the line direction as the angle of the field direction of the magnetic field generated by the magnetisation device in the region of the sensor line. The embodiment in which the magnetisation device comprises a single magnet permits a particularly compact and particularly straightforward structure of the measuring device.

In a preferred embodiment, a cavity open towards the sensor line is provided in the surface of a magnet of the magnetisation device, said surface facing the sensor line. It has been shown that, in the case of deviations from the cuboid shape—also able to be used according to a preferred embodiment—of a magnet of the magnetisation device, an essentially homogeneous magnetic field in the region of the sensor line with a field direction orientated in the region of the sensor line at an angle greater than 0° and less than 90° with respect to the sensor line can be generated particularly well. This embodiment is particularly preferably used with magnetisation devices which comprise a single magnet. It can however also offer advantages with magnetisation devices comprising a plurality of magnets. In a preferred embodiment, the cavity is constituted such that the opening of the cavity pointing towards the sensor line is larger than the area that the sensor line with its sensor elements itself occupies.

In a preferred embodiment, the opening of the cavity facing the sensor line is constituted rectangular. Particularly preferably, the length of the opening extends in the line direction and is greater than the width of the opening extending perpendicular to the line direction. It has been shown that, with such a cavity, an essentially homogeneous magnetic field in the region of the sensor line can be generated particularly well, the field direction whereof in the region of the sensor line forming an angle greater than 0° and less than 90° with respect to the line direction. In a preferred embodiment, the cavity has different depths. It has been shown that, with such a cavity, an essentially homogeneous magnetic field in the region of the sensor line can be generated particularly well, the field direction whereof in the region of the sensor line forming an angle greater than 0° and less than 90° with respect to the line direction. In a preferred embodiment, the cavity comprises a central region with a greater depth and lateral regions having a smaller depth arranged next to the central region in the line direction.

In a preferred embodiment, the cavity of the opening comprises mutually opposite base areas which particularly preferably are arranged in planes parallel to the plane of the opening. In a particularly preferred embodiment, each base area of the cavity is rectangular. To create an embodiment with varying depth, the individual base areas can be arranged at different distances from the plane of the opening. In a preferred embodiment, the cavity comprises a central base area farther away from the plane of the opening and, arranged beside this base area, one base area in one direction of the line direction and one in the opposite direction thereof, the latter being at a smaller distance from the plane of the opening. In a preferred embodiment, the cross-section of the cavity is mirror-symmetrical with respect to a plane containing the line direction and perpendicular to the plane of the opening. Such an embodiment of the cavity makes it possible, in a particularly favourable manner, to generate an essentially homogeneous magnetic field in the region of the sensor line, the field direction whereof in the region of the sensor line forming an angle greater than 0° and less than 90° with respect to the line direction.

In a preferred embodiment, the sensor elements directly or the chips carrying the sensor elements or the housing containing the chips are fixed on one side of a printed-circuit board and the measuring device is arranged on the opposite side of the printed-circuit board, particularly preferably fixed to the printed-circuit board. This embodiment makes it possible to bring the sensor elements particularly close to the measurement object to be examined, in particular the security document, or more precisely to bring the measurement plane, in which the object to be examined is moved in a preferred embodiment, close to the surface of the sensor elements.

In a preferred embodiment, a further sensor element not arranged in the sensor line is provided, which can measure the magnetic properties of its surroundings. This further sensor element is particularly preferably arranged between the magnetisation device and the sensor line or on the side of the magnetisation device lying opposite the sensor line. In a corresponding embodiment, the further sensor element can also be arranged in a cavity of a magnet of the magnetisation device that comprises a cavity. The provision of a further sensor makes it possible to measure interference fields, the origin whereof does not lie in the magnetic properties of the surroundings of the sensor line that are to be measured by the sensor line, particularly preferably are not generated by the security document to be examined in a preferred embodiment. The use of such a further sensor element makes it possible to eliminate from the signal generated by the sensor line the part that is attributable to interference fields.

In a preferred embodiment, the measuring device comprises an evaluation device. In the first place two, particularly preferably all the sensor elements particularly preferably comprise an output signal line, wherein in this preferred embodiment the output signal lines of the sensor elements can be led to the evaluation device. In a particularly preferred embodiment, the evaluation device can work out, per unit of time, the mean value from the signals of the output signal line of all the sensor elements. This embodiment is particularly well suited for applications of the measuring device according to the invention, wherein only the question of the presence of a magnetic property on a measurement object to be examined is to be verified, without for example ascertaining the specific position of a partial region on the measurement object giving rise to this magnetic property.

In a preferred embodiment, the sensor elements are arranged equidistant in the line direction. In a particularly preferred embodiment, the spacing of a first sensor element from an adjacent sensor element, related to the spacing between the centre-points of the two sensor elements, amounts to between 1 and 10 mm, preferably between 2 and 5 mm and particularly preferably to 3.5 mm. In a particularly preferred embodiment, a chip comprises two sensor elements arranged one after the other in the line direction and has—without the housing—a length of 1.5 to 9 mm, preferably of 2 to 3 mm and particularly preferably 2.5 mm in the line direction. In a preferred embodiment, the spacing from an edge of one chip to the edge of the neighbouring chip amounts to less than 1.5 mm and particularly preferably to less than 1.1 mm.

In an alternative embodiment, the sensor elements are arranged such that the spacing between the two edges of two adjacent sensor elements that are arranged on a chip is smaller than the spacing between two edges of adjacent sensor elements that are not arranged on a chip. The spacing between two chips is usually predetermined by the technology with which the chip can be connected to a carrier plate. These technologies usually require more space than the space that is required to arrange two magnetoresistive sensor elements on a chip. The sensitivity of the measuring device can thus be increased by the fact that the provision of the sensor elements on the chip and the provision of the chips on the board takes place as densely as possible according to the given technology used.

The production of the sensor elements on the chips preferably takes place with the methods of the planar technique, semiconductor technique or microsystem technique.

In a particularly preferred embodiment, the measuring device is constituted to detect magnetic structures of a note or a paper sheet, in particular a banknote, and comprises suitable means for moving the note or paper sheet past the sensor line in a measurement plane at least in a region close to the sensor line. Means suitable for this are in particular rollers, which form a roller gap between them, in which the note or the paper sheet can be held. If two groups of such rollers are used and the roller gaps formed between the rollers of the respective groups are suitably aligned with one another, a note or a paper sheet can be moved past the sensor line between the two roller groups in a plane. The note or paper sheet can also be moved past the sensor line lying on a conveyor belt, for example a conveyor belt having a rubber surface or a conveyor belt made of fleece.

In a preferred embodiment, the measuring device comprises two printed-circuit boards. The two printed-circuit boards are particularly preferably arranged parallel with one another. In the preferred embodiment, the first printed-circuit board can directly carry the sensor elements, or can carry chips which in turn carry the sensor elements. On the second printed-circuit board arranged particularly preferably parallel with the first printed-circuit board, a further sensor element not arranged in the sensor line can be provided. Furthermore, components of an evaluation device, for example preamplifiers for the output signals of the sensor elements, can be provided on this second printed-circuit board. In a preferred embodiment, the magnetisation device, particularly preferably the single magnet of the magnetisation device provided in a preferred embodiment, is arranged between the first printed-circuit board and the second printed-circuit board. In a correspondingly constituted preferred embodiment, a cavity provided in the magnet points with its opening towards the sensor line. The elements provided on the respective printed-circuit boards can be connected to one another by means of a flexible connection. In this preferred embodiment, a compact, virtually cuboid measuring device can be created as a result.

A possible area of application of the invention is the examination of notes or paper sheets, in particular banknotes, cheques or other paper sheets for the presence of magnetic features, in particular to establish whether the notes or paper sheets have particular, previously fixed magnetic features.

The measuring device according to the invention can be used in pattern recognition on security documents, such as for example banknotes, cheques, which are often provided with soft-magnetic and/or magnetic patterns. The device according to the invention can also be used in the recognition of so-called tags or in the recognition of magnetic barcodes. The measuring device according to the invention can also be used in material testing, such as for example in the ascertainment of faults, holes or cracks in ferromagnetic or electrically conductive materials. The measuring device according to the invention can also be used with magnetic arrays in biochips or in the so-called "Lab-on-a-Chip" technology, for example to verify magnetic beads or to homogenise the sensitivity distribution of the array. In particular, the measuring device according to the invention can be used as a substitute for inductive heads.

BRIEF DESCRIPTION OF THE DRAWINGS

The invention is explained below in greater detail with the aid of a drawing merely representing examples of embodiment of the invention. In the figures.

DETAILED DESCRIPTION

Figure 1:
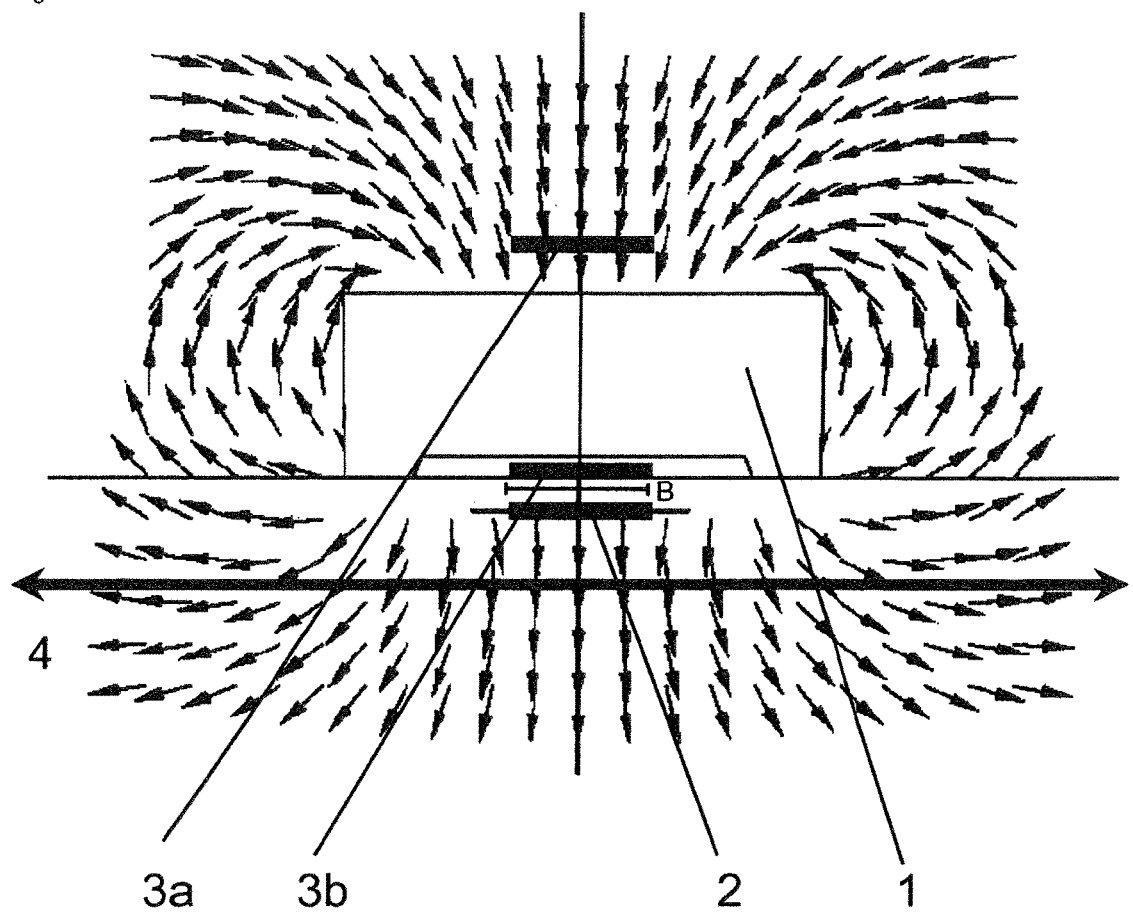
FIG. 1: shows a diagrammatic side view of the sensor line and a magnetisation device of the measuring device according to the invention constituted with a single magnet as a cross-section perpendicular to the line direction.
Figure 2:
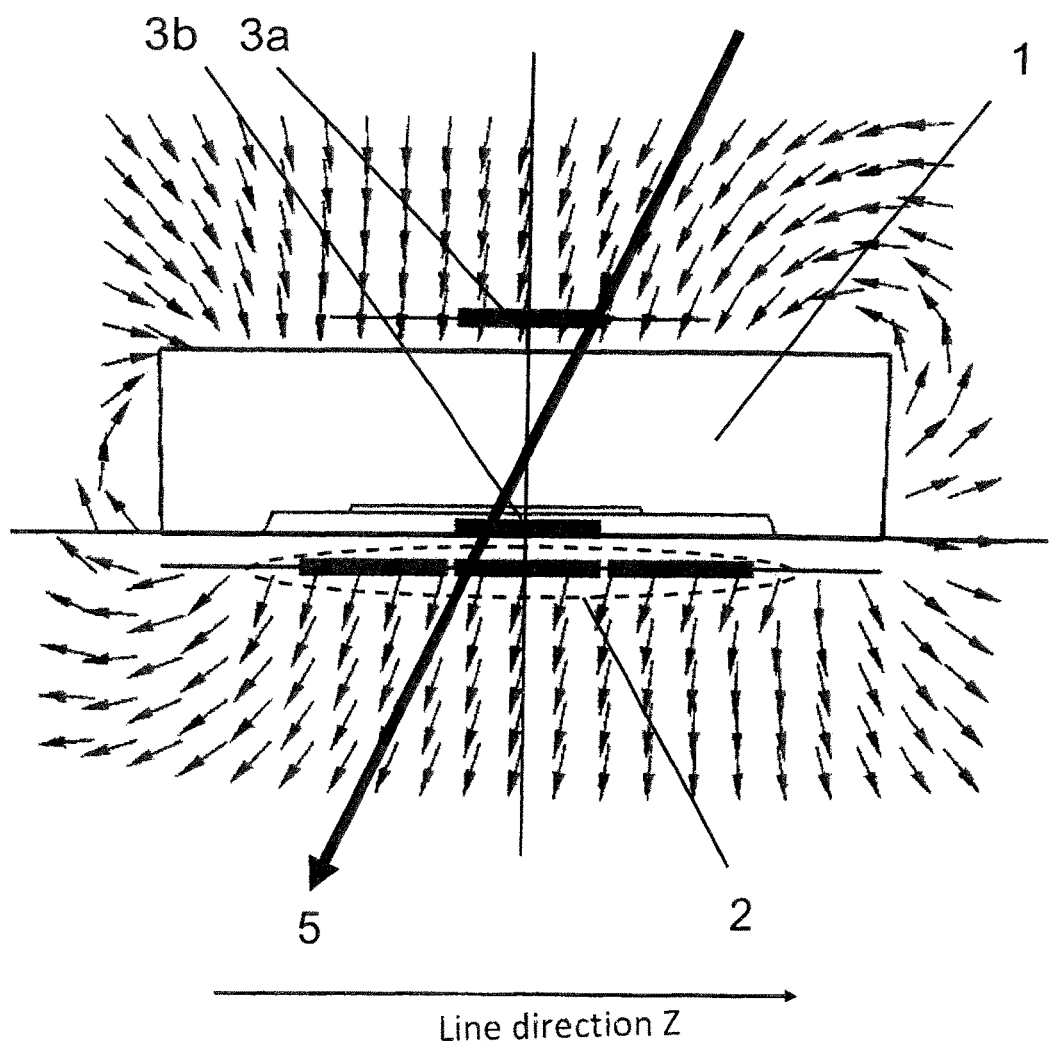
FIG. 2: shows a diagrammatic front view of the components of the measuring device according to the invention represented in FIG. 1 as a cross-section perpendicular to the line direction.

The embodiments of the measuring device according to the invention represented in the figures for the measurement of magnetic properties of the surroundings of the measuring device comprise a sensor line 2 with at least two sensor elements 7 extending in a line direction Z. The magnetic properties of the surroundings of the measuring device can be measured with sensor line 2. The measuring device according to the invention comprises a magnetisation device, which comprises either (FIG. 1-6) a single magnet 1 or (FIG. 8) two magnets 11 or (FIG. 9) four magnets 11. FIG. 2 shows that the magnetic field generated by the magnetisation device is essentially homogeneous in the region of the sensor line and its field direction in the region of the sensor line forms an angle of $\alpha=65°-85°$ with respect to line direction Z. FIG. 1 shows that the magnetic field generated by the magnetisation device has essentially no component that points perpendicular to the line direction in the direction of width B of the sensor elements.

FIGS. 1 to 6 show that the magnetisation device comprises a single magnet 1. FIG. 2 shows that the length of magnet 1 extends beyond the length of the sensor line.

Figure 3:
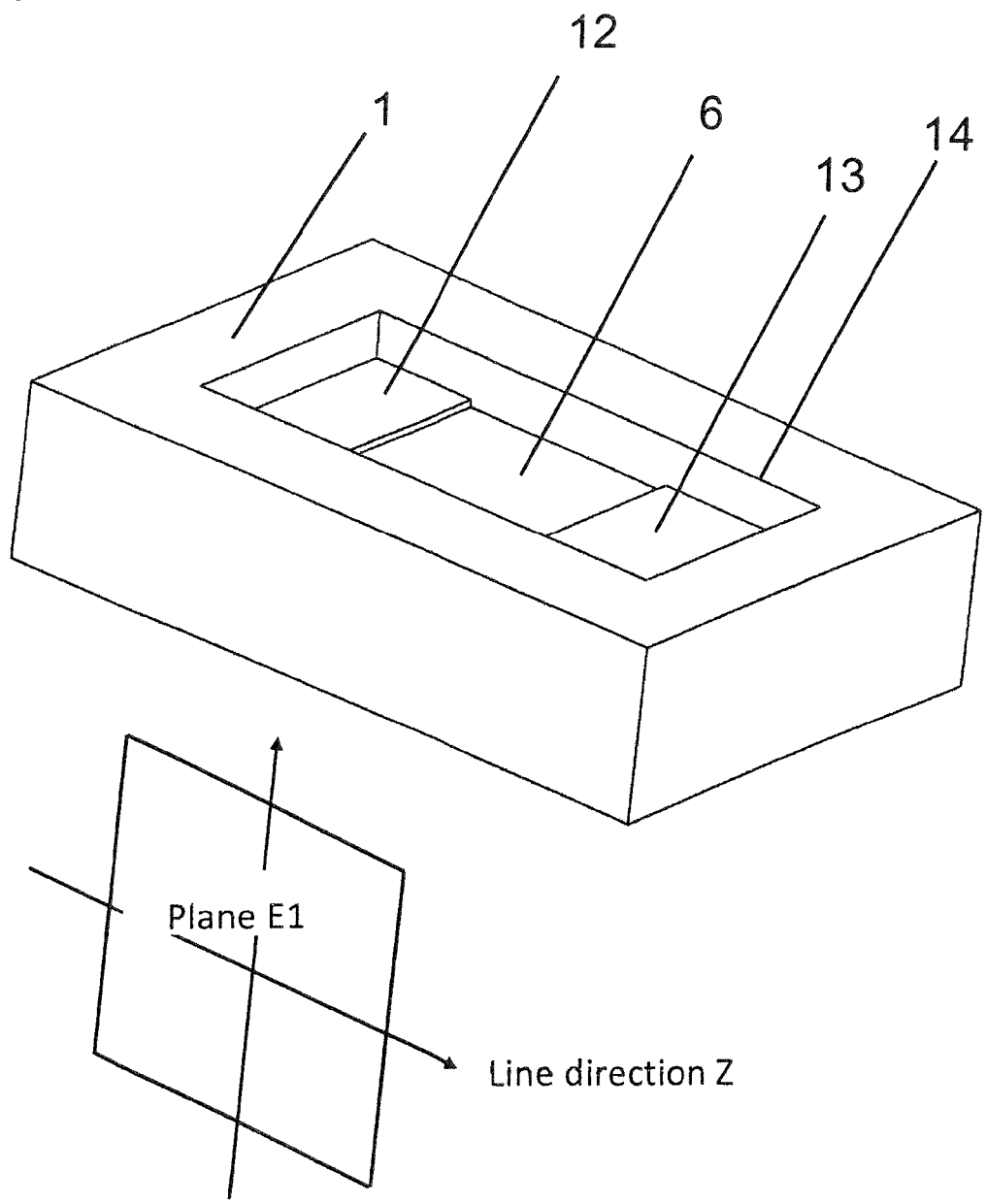
FIG. 3: shows a diagrammatic, perspective view of the magnet of the magnetisation device of the embodiment of FIGS. 1 and 2.

In single magnet 1 of the magnetisation device, there is provided in its surface facing sensor line 2 a cavity 14 open towards the sensor line (FIG. 3). Cavity 14 has an essentially rectangular opening. Furthermore, cavity 14 comprises a centrally arranged base area 6 and two further base areas 12, 13 each arranged beside base area 6 in the line direction (see FIG. 3). In the perspective view of FIG. 3, it can also be seen that the depth of the cavity is deeper in the region of central base area 6 than in the region of base areas 12, 13 arranged beside the latter.

It can further be seen in FIG. 3 that the cross-section of cavity 14 is mirror-symmetrical in a plane E1 which also contains line direction Z and lies perpendicular to the plane of the cavity.

Figure 4:
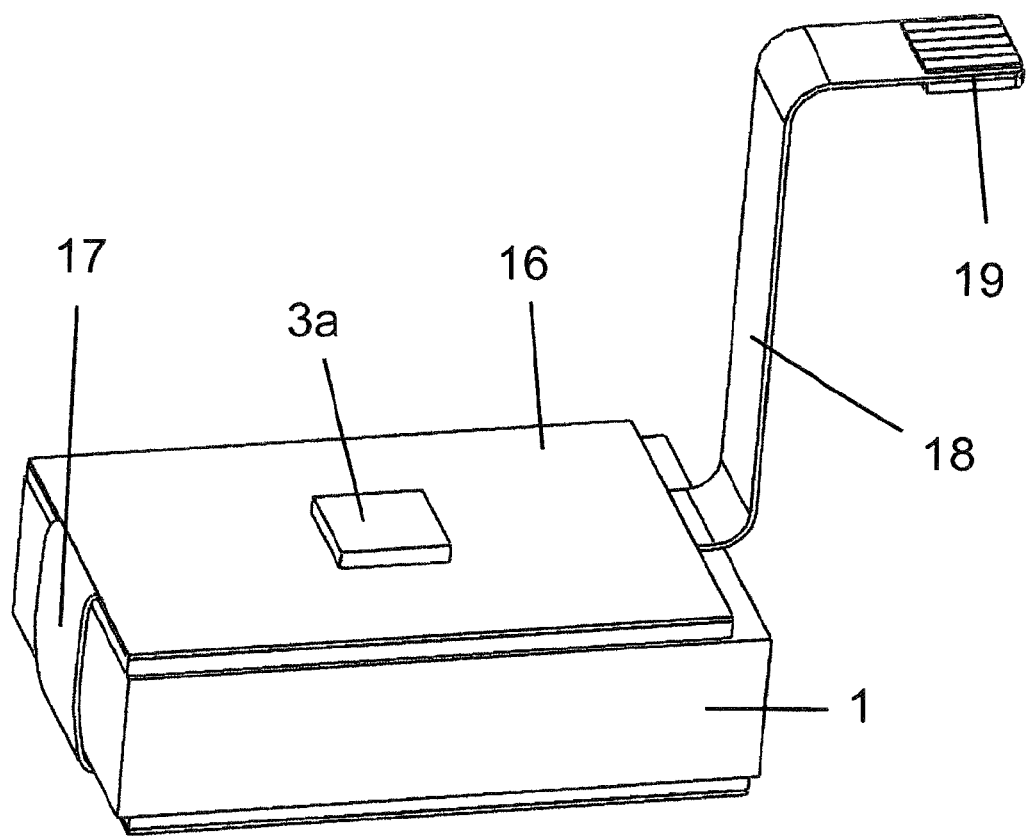
FIG. 4: shows a diagrammatic, perspective view from above of the measuring device according to the invention.
Figure 5:
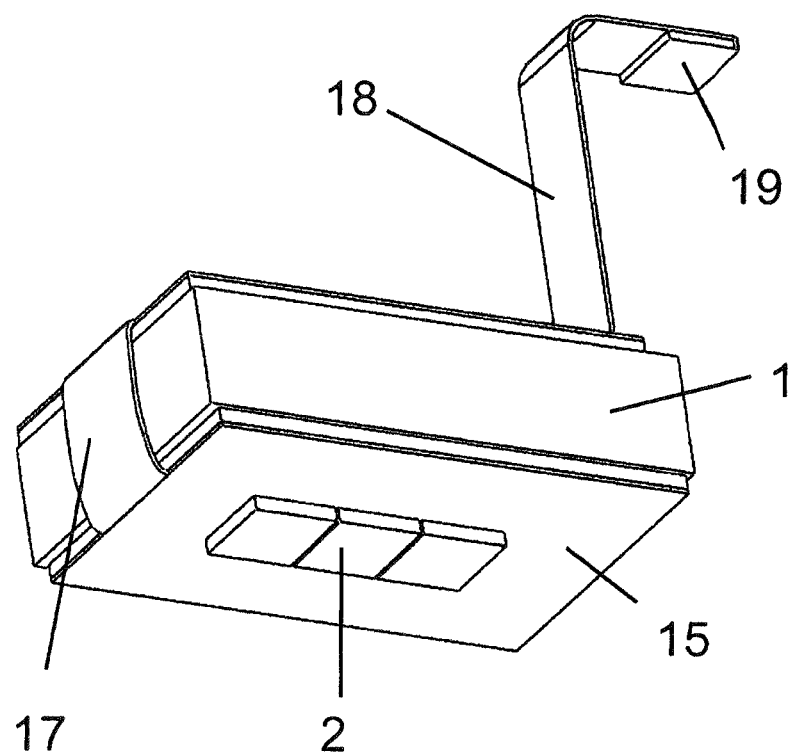
FIG. 5: shows a diagrammatic, perspective view from below of the measuring device according to the invention.
Figure 6:
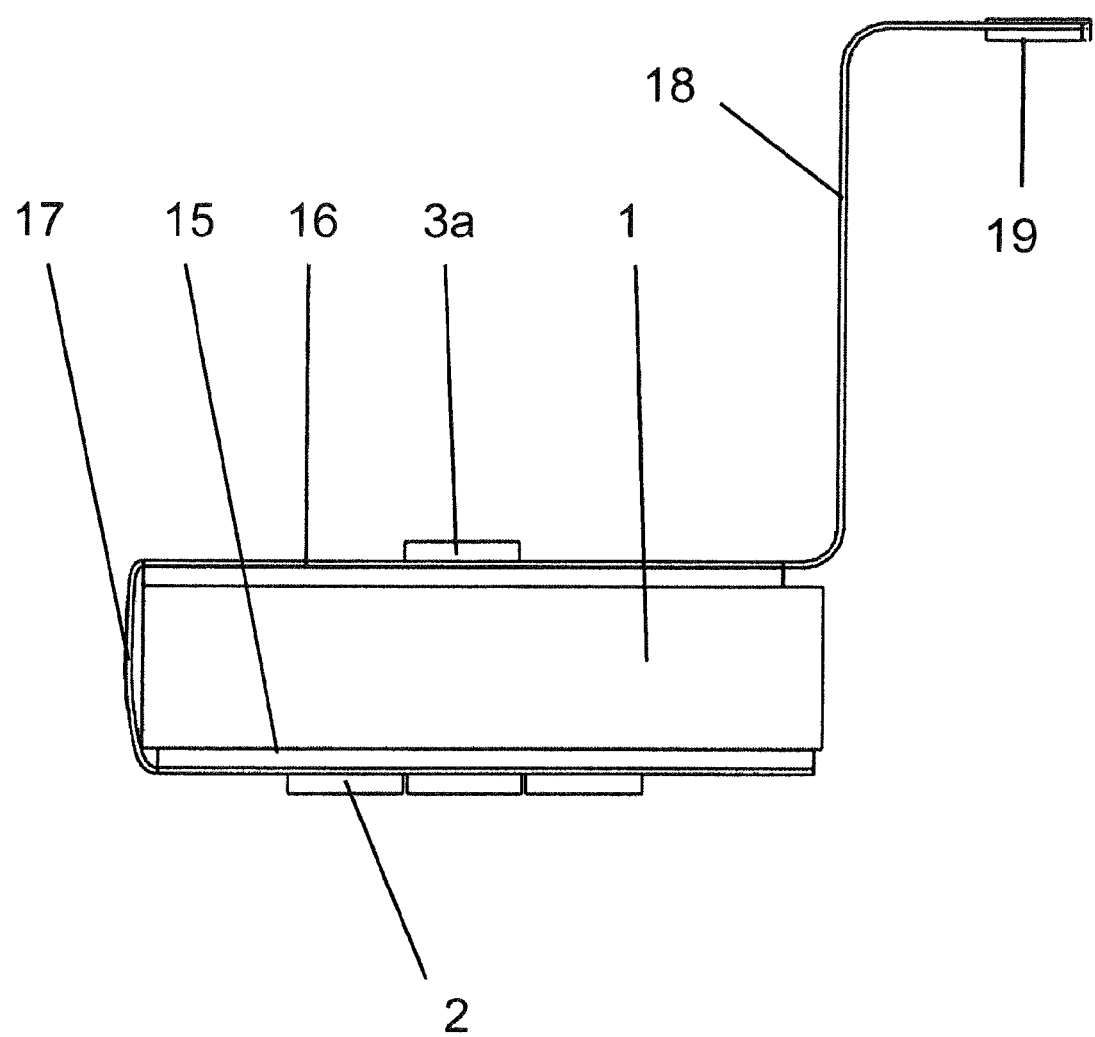
FIG. 6: shows a diagrammatic side view of the measuring device according to the invention.

FIGS. 4, 5, 6 show that the measuring device according to the invention comprises two rigid printed-circuit board parts connected by a flexible section 17. FIG. 5 shows that the sensor housings containing the sensor elements in sensor line 2 are fixed to a first printed-circuit board part 15. FIG. 4 shows a further sensor 3a, which is not arranged in sensor line 2 and which contains further sensor elements and is fixed to a second printed-circuit board part 16. It can further be seen from FIGS. 4, 5 and 6 that single magnet 1 of the magnetisation device is arranged between printed-circuit board parts 15, 16 arranged in parallel. FIGS. 4, 5 and 6 also show that a flexible connection 17 connects first printed-circuit board part 15 to second printed-circuit board part 16. A second flexible connection 18 connects second printed-circuit board part 16 to a connection plug 19.

FIGS. 1 and 2 show that further sensor elements 3a, 3b not arranged in the sensor line can be provided, which can measure the magnetic properties of their surroundings. Further sensor element 3b is arranged in the cavity of magnet 1. Further sensor element 3a is arranged on the side of the magnetisation device lying opposite the sensor line. Further sensor elements 3a, 3b can also be provided as an alternative to one another or can also be omitted in other embodiments of the invention.

Further components of an evaluation device can be provided on printed-circuit board 16. Output signal lines of the sensor elements can be connected via flexible connection 17 to these components of an evaluation device. The evaluation device can then work out, per unit of time, the mean value from the signals of the output signal lines of the sensor elements of the sensor line and/or preamplify the signals and/or carry out a digitalisation.

Figure 7:
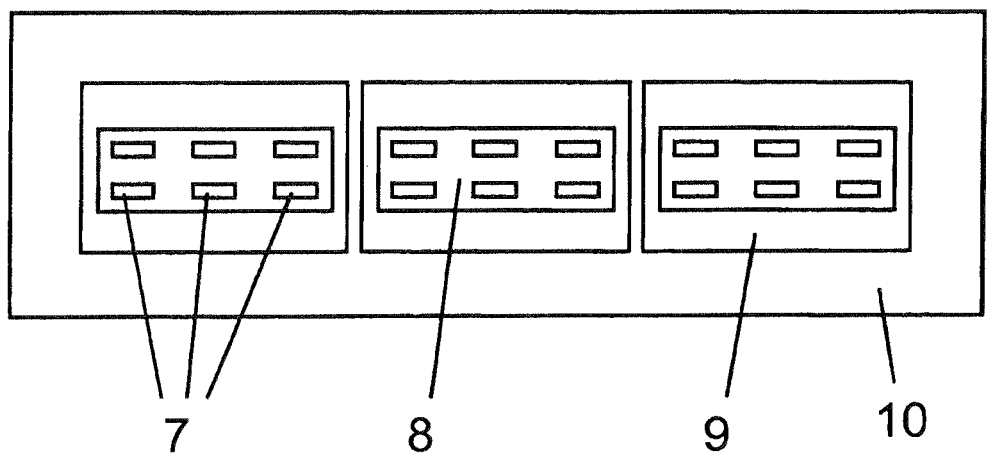
FIG. 7: shows a diagrammatic view of the sensor line of the measuring device according to the invention.

FIG. 7 shows diagrammatically the typical structure of a sensor line 2 according to the invention comprising sensor housings 9 soldered on a printed-circuit board 10, which each contain a chip 8 which in turn is a carrier of a number of magnetic field-sensitive sensor elements 7.

Figure 8:
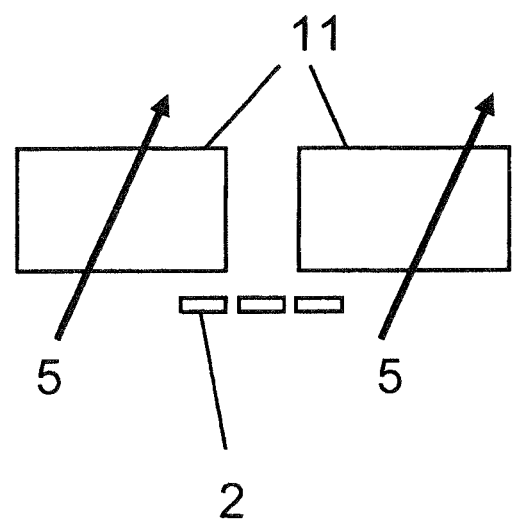
FIG. 8: shows a diagrammatic side view of a measuring device according to the invention constituted with two separate magnets

FIG. 8 shows an embodiment according to the invention, wherein, instead of a single magnet, two obliquely magnetised magnets 11 are used for the generation of a support field and premagnetisation field in the region of sensor line 2, said support field and premagnetisation field in particular being homogeneous in the line length direction.

Figure 9:
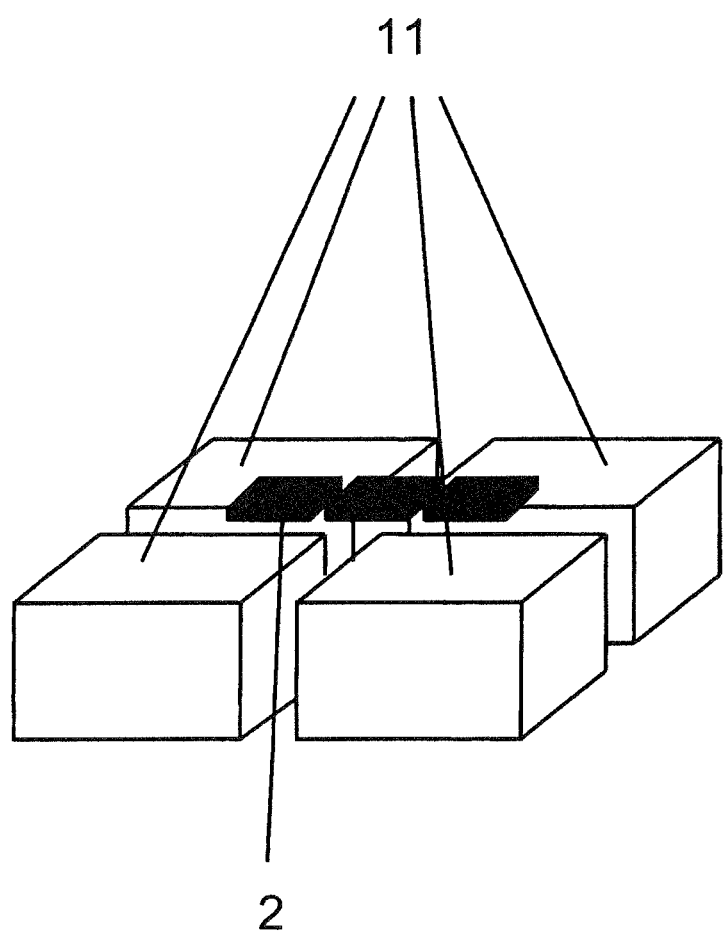
FIG. 9: shows a diagrammatic, perspective view of a measuring device according to the invention constituted by 4 individual magnets.

FIG. 9 shows a further embodiment, wherein a further homogenisation of the field in the line region in the direction perpendicular to the line length direction is achieved by further splitting-up of the two magnets from FIG. 8 into a total of 4 magnets 11.

The invention claimed is:

1. A measuring device for measuring magnetic properties of the surroundings of the measuring device comprising:
   a sensor line with at least two sensor elements for detecting magnetic field properties extending in a direction of said sensor line; and
   a magnetisation device configured to generate a magnetic field, said magnetic field being essentially homogeneous in a region of the sensor line and having a field direction that forms an angle of greater than 0° and less than 90° with respect to the direction of said sensor line,
   wherein said sensor line has a length, a width and a height, wherein the height is less than the width and the height is less than the length, wherein the magnetic field generated by the magnetisation device in the region of the sensor line has essentially only one field component in the direction of the length of the sensor line and one field component in the direction of the height of the sensor line, and essentially no field component in the direction of the width of the sensor line.

2. The measuring device of claim 1, the magnetisation device comprising:
   a first magnet, arranged in the direction of the sensor line in a region of a first end of the sensor line, and
   a second magnet arranged in the direction of the sensor line in a region of a second end of the sensor line opposite said first end, wherein the first magnet and the second magnet have magnetisation directions that form an angle of greater than 0° and less than 90° with respect to the direction of the sensor line.

3. The measuring device of claim 2, wherein the first magnet comprises two individual magnets separated by an intermediate space and wherein the second magnet comprises two other individual magnets separated by an intermediate space.

4. The measuring device of claim 1, wherein the magnetisation device comprises a single magnet, which extends at least over the entire length of the sensor line in the direction of the sensor line and which is arranged such that the line connecting a north pole of the magnetisation device to a south pole of the magnetisation device forms an angle of greater than 0° and less than 90° with respect to the direction of the sensor line.

5. The measuring device of claim 4, further comprising:
   a cavity defined in the surface of the single magnet facing the sensor line.

6. The measuring device of claim 5, wherein the cavity facing the sensor line defines an opening that is rectangular and the length of the opening extending in the direction of the sensor line is longer than the width of the opening extending perpendicular to the direction of the sensor line.

7. The measuring device of claim 5, wherein the cavity has different depths.

8. The measuring device of claim 5, wherein a cross-section of the cavity is mirror-symmetrical with respect to a plane containing the direction of the sensor line.

9. The measuring device of claim 1, wherein the sensor elements are fixed on a first side of a printed-circuit board and the magnetisation device is arranged on an opposite side of the printed-circuit board.

10. The measuring device of claim 1, further comprising:
    an additional sensor element not arranged in the sensor line configured to measure the magnetic properties of its surroundings.

11. The measuring device of claim 1, further comprising:
    an evaluation device, wherein the least two sensor elements of the sensor line comprise an output signal line and the output signal lines of the sensor elements of the sensor line are in electrical communication with the evaluation device and the evaluation device calculates, per unit of time, the mean value of signals from the output signal lines of the sensor elements of the sensor line.

12. The measuring device of claim 10, wherein the additional sensor element is arranged between the magnetisation device and the sensor line.

13. The measuring device of claim 9, wherein the magnetisation device is attached to the opposite side of the printed-circuit board.

14. The measuring device of claim 9, wherein the sensor elements are fixed directly on the first side of the printed-circuit board.

15. The measuring device of claim 9, wherein the sensor elements are carried on chips, the chips being fixed to the first side of the printed-circuit board.

16. The measuring device of claim 1, wherein the field direction of the magnetic field forms an angle that is greater than 0° and less than 85° relative to the direction of the sensor line.

17. The measuring device of claim 1, wherein the field direction of the magnetic field forms an angle that is greater than 45° and less than 85° relative to the direction of the sensor line.

18. A method for detecting magnetic features of an article, comprising the steps of:
    generating an essentially homogeneous magnetic field having a field direction that forms an angle that is greater than 0° and less than 90° relative to a direction of a sensor line comprising at least two sensor elements arranged in a direction of the sensor line;
    passing the article proximal to the sensor line and in the magnetic field; and
    detecting, by the sensor elements, a change in the magnetic field responsive to the passing of the article,
    wherein said sensor line has a length, a width and a height, wherein the height is less than the width and the height is less than the length, wherein the generated magnetic field has essentially only one field component in the direction of the length of the sensor line and one field component in the direction of the height of the sensor line, and essentially no field component in the direction of the width of the sensor line.

19. The method of claim 18, wherein the field direction of the magnetic field forms an angle that is greater than 0° and less than 85° relative to the direction of the sensor line.

* * * * *